US012802778B2

(12) United States Patent
Yu et al.

(10) Patent No.: US 12,802,778 B2
(45) Date of Patent: Nov. 17, 2026

(54) REVERSE VIRTUAL SCREENING PLATFORM AND METHOD BASED ON PROGRAMMABLE QUANTUM COMPUTING

(71) Applicant: ZHEJIANG LAB, Hangzhou (CN)

(72) Inventors: Shang Yu, Hangzhou (CN); Zhipeng Zhong, Hangzhou (CN); Liang Xu, Hangzhou (CN); Jianshun Tang, Hangzhou (CN); Yitao Wang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 799 days.

(21) Appl. No.: 18/122,251

(22) Filed: Mar. 16, 2023

(65) Prior Publication Data

US 2024/0038325 A1 Feb. 1, 2024

Related U.S. Application Data

(63) Continuation of application No. PCT/CN2022/116170, filed on Aug. 31, 2022.

(30) Foreign Application Priority Data

Jul. 26, 2022 (CN) ........................ 202210881335.3

(51) Int. Cl.
*G16B 15/30* (2019.01)
*G06N 10/20* (2022.01)
*G16C 10/00* (2019.01)

(52) U.S. Cl.
CPC ............. *G16B 15/30* (2019.02); *G06N 10/20* (2022.01); *G16C 10/00* (2019.02)

(58) Field of Classification Search
CPC ........ G16B 15/30; G06N 10/20; G06N 10/40; G16C 10/00
See application file for complete search history.

(56) References Cited

U.S. PATENT DOCUMENTS

2022/0051124 A1 2/2022 Bradler et al.
2022/0101168 A1 3/2022 Bourassa et al.
2023/0177374 A1* 6/2023 Bradler .................. G06N 10/60 359/107

FOREIGN PATENT DOCUMENTS

CA 3139835 A1 11/2020
CN 105678112 A 6/2016
(Continued)

OTHER PUBLICATIONS

Molecular docking with Gaussian Boson Sampling (Year: 2020).*
(Continued)

*Primary Examiner* — Pei Yong Weng
(74) *Attorney, Agent, or Firm* — IPro, PLLC

(57) ABSTRACT

The application discloses a reverse virtual screening platform and method based on programmable quantum computing, the method includes the following steps: S1, for a given micromolecule and a target protein molecule, calculating a binding interaction graph of the given micromolecule and the target protein molecule on a computer according to different distances between pharmacophores; S2, encoding, according to an adjacency matrix of the binding interaction graph, the binding interaction graph into a quantum reverse virtual screening platform by decomposing the adjacency matrix; and S3, performing Gaussian boson sampling by the quantum reverse virtual screening platform. The reverse virtual screening platform and method based on programmable quantum computing provided by the present application are implemented by an optical quantum computer system based on a time domain.

5 Claims, 4 Drawing Sheets

(56) References Cited

FOREIGN PATENT DOCUMENTS

| | | | |
|---|---|---|---|
| CN | 108919281 | A | 11/2018 |
| CN | 111783990 | A | 10/2020 |
| CN | 113225184 | A | 8/2021 |
| CN | 113853563 | A | 12/2021 |
| CN | 114219694 | A | 3/2022 |
| CN | 216352386 | U | 4/2022 |
| CN | 114566233 | A | 5/2022 |
| CN | 114600015 | A | 6/2022 |
| WO | 0175495 | A2 | 10/2001 |
| WO | 2004042965 | A2 | 5/2004 |

OTHER PUBLICATIONS

An investigation of doubly-resonant optical parametric oscillators and nonlinear crystals for squeezing (Year: 2010).*

Hu Yi. "Research on the Technology of Photon Coincidence Counting and Laser Phase Locking." A dissertation for doctor's degree. University of Science and Technology of China. Jun. 30, 2020.

Yang, Zelin, et al. "Synthesis and identification of a novel derivative of salidroside as a selective, competitive inhibitor of monoamine oxidase B with enhanced neuroprotective properties." European journal of medicinal chemistry 209 (2021): 112935.

Banchi, Leonardo, et al. "Molecular docking with Gaussian boson sampling." Science advances 6.23 (2020): eaax1950.

Hoch, Francesco, et al. "Boson sampling in a reconfigurable continuously-coupled 3d photonic circuit." arXiv preprint arXiv:2106.08260 (2021).

Craig S. Hamilton, et al. "Gaussian Boson Sampling." arXiv:1612.01199v1 [quant-ph] Dec. 4, 2016.

Nussbaum, Benjamin E., et al. "Design methodologies for integrated quantum frequency processors." arXiv:2204.12320v1 [quant-ph] Apr. 26, 2022.

Arrazola, Juan M., et al. "Quantum circuits with many photons on a programmable nanophotonic chip." Nature 591.7848 (2021): 54-60.

Zhong, Han-Sen, et al. "Phase-programmable gaussian boson sampling using stimulated squeezed light." Physical review letters 127.18 (2021): 180502.

Pant, Mihir, and Dirk Englund. "Efficient Boson Sampling schemes using dispersion and pulse shaping." 2015 Conference on Lasers and Electro-Optics (CLEO). IEEE, 2015.

DE11 2022 000 041.4 First Office Action, issued on Sep. 29, 2025.

* cited by examiner

REVERSE VIRTUAL SCREENING PLATFORM AND METHOD BASED ON PROGRAMMABLE QUANTUM COMPUTING

CROSS REFERENCE TO RELATED APPLICATIONS

The present application claims priority of Chinese patent application No. 202210881335.3 filed with the China National Intellectual Property Administration on Jul. 26, 2022 and entitled "Reverse Virtual Screening Platform and Method based on Programmable Quantum Computing", the entire content of which is incorporated herein by reference.

TECHNICAL FIELD

The present application relates to the technical field of drug design based on a quantum algorithm, in particular, to a reverse virtual screening platform and method based on programmable quantum computing.

BACKGROUND

Computer-aided drug design is now widely used to discover new bioactive molecules. As a structure-based drug design method, molecular docking can be used to predict optimal binding sites between ligands and receptors. It turns out that if the docking problem is explained using a process of finding a maximum weighted complete subgraph, docking can be completed by a Gaussian boson sampling experiment. This sampling experiment can perform quantum sampling tasks that are difficult to achieve by classical methods.

SUMMARY

The present application aims to provide a reverse virtual screening platform and method based on programmable quantum computing, so as to overcome the shortcomings in the prior art.

In order to achieve the above purposes, the present application provides the following technical solution.

The present application provides a reverse virtual screening method based on programmable quantum computing, including the following steps:

S1, for a given micromolecule and a target protein molecule, calculating a binding interaction graph of the given micromolecule and the target protein molecule on a computer according to different distances between pharmacophores;

S2, encoding, according to an adjacency matrix of the binding interaction graph, the binding interaction graph into a quantum reverse virtual screening platform by decomposing the adjacency matrix;

S3, performing Gaussian boson sampling by the quantum reverse virtual screening platform, specifically including the following sub-steps:

S31, chopping pulse laser by using an acoustic optical modulator, pumping a nonlinear crystal to obtain a group of single-mode squeezed vacuum states with different squeezing degrees, and delivering the single-mode squeezed vacuum states into a circulating light path of a quantum processing unit module;

S32, performing a high-dimensional global unitary evolution operation by electro-optical modulators in the circulating light path, and inputting an evolution result into a detection module, wherein there are two electro-optical modulators, the electro-optical modulators are equipped with power amplifiers capable of amplifying an analog signal and are controlled by a programmable arbitrary waveform generator;

S33, measuring a photon number in each mode by a superconducting single-photon detector in the detection module, and inputting a measurement result into a computer to obtain a sampling result processed by a quantum algorithm; and S4, obtaining all fully connected subgraphs of the binding interaction graph according to the sampling result, and sorting all the fully connected subgraphs according to weights to obtain a fully connected subgraph with a maximum weight, so as to directly determine an optimal connection manner for the micromolecule and the target protein molecule by a structure of the fully connected subgraph with the maximum weight.

The present application discloses a reverse virtual screening platform based on programmable quantum computing, including a light source preparation module, a quantum processing unit module, a detection module, and a computer;

the light source preparation module includes a mode-locked pulse laser light source, an acoustic optical modulator, and a nonlinear crystal; pulse laser generated by the mode-locked pulse laser light source is chopped by the acoustic optical modulator, and the nonlinear crystal is pumped to finally obtain a group of single-mode squeezed vacuum states with different squeezing degrees; the single-mode squeezed vacuum states are delivered into the quantum processing unit module;

the quantum processing unit module is a circulating light path where a polarization beam splitter, a first electro-optical modulator, a polarization delay device, an arbitrary unitary operation module, a second electro-optical modulator, and a time delay module are disposed in sequence; the arbitrary unitary operation module is controlled by a programmable arbitrary waveform generator; the quantum processing unit module controls the squeezed states to be continuously evolved in the circulating light path until a high-dimensional unitary operation in any mode is completed, and delivers an evolution-completed squeezed state sequence into the detection module;

the detection module measures a photon number in each mode by a superconducting nanowire single-photon detector, and inputs a measurement result into the computer; and the computer encodes a task to be a sequence of a string of instructions to control the arbitrary waveform generator, thus controlling a quantum logic gate sequence of the screening platform and realizing a programmable function; and the computer is used for performing real-time display, record and analysis on the photon number detected by the single-photon detector.

Preferably, in the light source preparation module, the mode-locked pulse laser light source outputs high-energy pulse light to pump the nonlinear crystal to provide an optical quantum computer system with a light source for preparing the squeezed states, and is located at an initial position of the light source preparation module; the acoustic optical modulator is used for selecting a laser pulse to obtain a repetition frequency and pulse number of a desired laser pulse; the nonlinear crystal is pumped by the mode-locked pulse laser light source to generate the corresponding squeezed states, so that the optical quantum computer system completes a Gaussian Boson sampling task; and the nonlinear crystal is placed behind the mode-locked pulse laser light source in the light source preparation module.

Preferably, a specific preparation method for a squeezed state sequence of the light source preparation module is as follows: chopping the pulse laser generated by the mode-locked pulse laser light source via the acoustic optical modulator to form a sequence composed of n pulses; adjusting the pulse energy of the sequence via the electro-optical modulator, and modulating and shaping the spectrum of the sequence via a spatial filter composed of a grating, a cylindrical lens and a spatial light modulator; delivering the sequence finally into the nonlinear crystal to generate corresponding dual-mode squeezed vacuum states; then, performing polarization transformation on the dual-mode squeezed vacuum states, and enabling the dual-mode squeezed vacuum states to become single-mode squeezed vacuum states with the same squeezing degree as the dual-mode squeezed vacuum states by a non-polarizing beam splitter; filtering pumped light by a filter; and finally, delivering the squeezed states into the quantum processing unit module.

Preferably, in the light source preparation module, a level signal of a pulse laser device that is synchronized with the pulse sequence may be directly used as a time reference for subsequent device regulation and control.

Preferably, in the quantum processing unit module, the first electro-optical modulator is used for controlling polarization of light; and the first electro-optical modulator respectively adjusts the polarization of the light to be in a horizontal or vertical state according to a state of the level signal, and further controls various modes of squeezing for entry into different light paths to achieve different operations.

Preferably, the squeezed state sequence is delayed by the time delay module to obtain delay-time having a corresponding length; and after the evolution of the last mode in the pulse or squeezed state sequence is completed, the sequence enters a next evolution stage to ensure that the evolution is not disordered in timing.

Preferably, the polarization delay device is used for delaying a vertical or horizontal polarization component in a squeezed state in each mode such that the horizontal and vertical polarization components in the squeezed state sequence are separated and that two adjacent modes may overlap in time after being delayed on the polarization delay device, so as to achieve a unitary operation for the two adjacent modes.

Preferably, the second electro-optical modulator in the circulating light path is used for controlling the number of cycles of the pulse or squeezed state sequence in an annular light path; and by controlling the polarization of the light, the pulse or squeezed state sequence is controlled to continue the evolution in the annular light path or to enter the detection module from the circulating light path.

Preferably, the arbitrary unitary operation module includes two electro-optical modulators controlled by the arbitrary waveform generator; the arbitrary waveform generator generates a level-tunable signal and inputs the signal into voltage amplifiers which are equipped for the electro-optical modulators and are capable of amplifying an analog signal; the amplifiers linearly amplify the level signal generated by the arbitrary waveform generator, and control the electro-optical modulators to perform continuously tuned phase modulation between two polarizations of a light signal; and the electro-optical modulators quickly adjust phases of the squeezed states in each mode, and achieve an arbitrary unitary operation between two adjacent modes.

Preferably, in the detection module, the superconducting nanowire single-photon detector is used for detecting, in response to a single-photon signal, that there are modes with one or more photons after evolution; a coincidence instrument performs coincidence processing on a level detection signal output by the superconducting single-photon detector and a level detection signal output by a photoelectric detector in the light source preparation module or a level synchronization signal output by the pulse laser device; the time of arrival at the detector is changed according to different evolution lengths of the pulse or squeezed state sequence in the annular light source; and during the coincidence processing, the level signal for triggering is delayed for a corresponding duration in a circuit setting.

Preferably, the superconducting nanowire single-photon detector is connected to two signal input ports of the coincidence instrument respectively, and the level signal generated in the light source preparation module is used for coincidence triggering, so as to reduce the interference of noise; and the coincidence instrument is connected to the computer, and obtains, by means of analyzing whether a photon exists in each time mode, a Gaussian boson sampling computation result.

The present application has the following beneficial effects. The reverse virtual screening platform and method based on the programmable quantum computing provided by the present application are implemented by a time domain-based optical quantum computer system. The time domain-based optical quantum computer system adopts the circulating light path, so that the process cost of large-scale preparation of quantum computers is reduced, and it is convenient for construction on an optical platform; and the optical quantum computer system is stable in structure and easily extends the number of mode bits. Meanwhile, the screening platform can be operated in a room-temperature atmospheric environment; and electro-optical modulation elements in the screening platform can be controlled by the computer to implement more quantum algorithms and quantum simulation tasks. By encoding the squeezed states in the time domain, compared with other quantum computer systems, such as a superconducting quantum system, an ion trap system, and an optical integrated chip system, the present application has relatively high extensibility in aspects of quantum state preparation, quantum state regulation and control, and quantum state detection, and has relatively low manufacturing cost. The present application has the outstanding advantages of extensible dimension (number of bits), programmable control, operation in a room-temperature environment, high stability, and the like.

DETAILED DESCRIPTION

Figure 1:
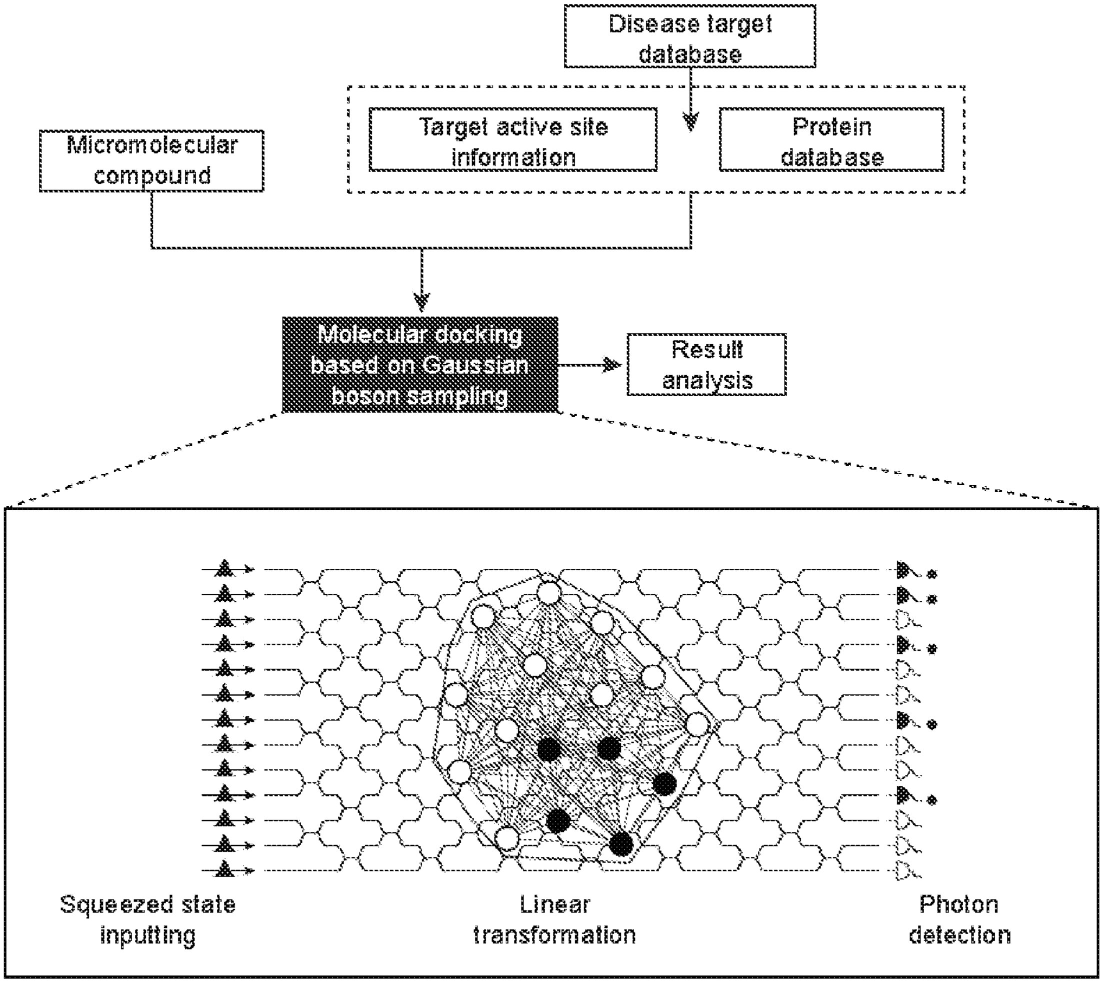
FIG. 1 is a logic principle diagram according to an embodiment of the present application.

In order to make the objectives, technical solutions and advantages of the present application clearer, the present application is further described below in detail with reference to accompanying drawings and embodiments. It should be understood that the specific embodiments described here are merely to explain the present application, and are not intended to limit the scope of the present application. In addition, in the following descriptions, the descriptions of known structures and techniques are omitted to avoid unnecessary confusion of the concept of the present application.

An embodiment of the present application provides a reverse virtual screening platform based on programmable quantum computing, which is used for Gaussian boson sampling. The Gaussian boson sampling can quickly and effectively complete a molecular connection task, so that a molecular connection module with high hashrate consumption in the traditional reverse virtual screening platform can be replaced to increase the computation speed of drug design. The Gaussian boson sampling in the present application is completed in an optical quantum computer system based on a time domain. Squeezed states that are discrete in the time domain can be generated by chopping pulse laser and pumping a nonlinear crystal, and meanwhile, optical quantum bits input into a quantum computer can be encoded on the time domain. The number of evolutions, in the light path, of the squeezed states entering an annular light path may be controlled by electro-optical modulators equipped with power amplifiers capable of amplifying a digital signal and an acoustic optical modulator. The two electro-optical modulators equipped with power amplifiers capable of amplifying an analog signal in the annular light path may be controlled to perform encoding by an arbitrary waveform generator and may achieve an arbitrary SU(2) operation between two adjacency mode bits and finally complete a high-dimensional unitary operation of any mode. A superconducting nanowire single-photon detector placed at the end can be used for detecting an event whether there is a photon in each mode on the time domain; and these measurement results will be input into a computer, and a result is obtained by calculation by assistance of a corresponding program. This set of photonic quantum computing system can be operated in a room-temperature atmospheric environment, and is easy to mount and remove; an output waveform of the arbitrary waveform generator is controlled by programming, so as to encode information by any molecules; and meanwhile, the extensibility of the quantum computer system is greatly improved by a time domain encoding manner. The reverse virtual screening platform based on programmable quantum computing has the advantages of dimension (number of bits) extensibility, programmable control, operation in the room-temperature atmospheric environment, high stability and the like. The reverse virtual screening platform can be used for molecular connection-based drug design projects.

As shown in FIG. 1, a binding interaction graph composed of m vertexes is formed by a micromolecule compound provided by a user to be inquired and proteins in disease target database. An optimal molecular docking result can be found by searching a maximum fully connected subgraph of the binding interaction graph. The binding interaction graph is encoded into a Gaussian boson sampling machine, and the maximum fully connected subgraph is searched using a sampling result. Compared with a classical sampling molecular docking method, the molecular docking based on Gaussian boson sampling can greatly improve the docking success rate and the computation speed.

Figure 2:
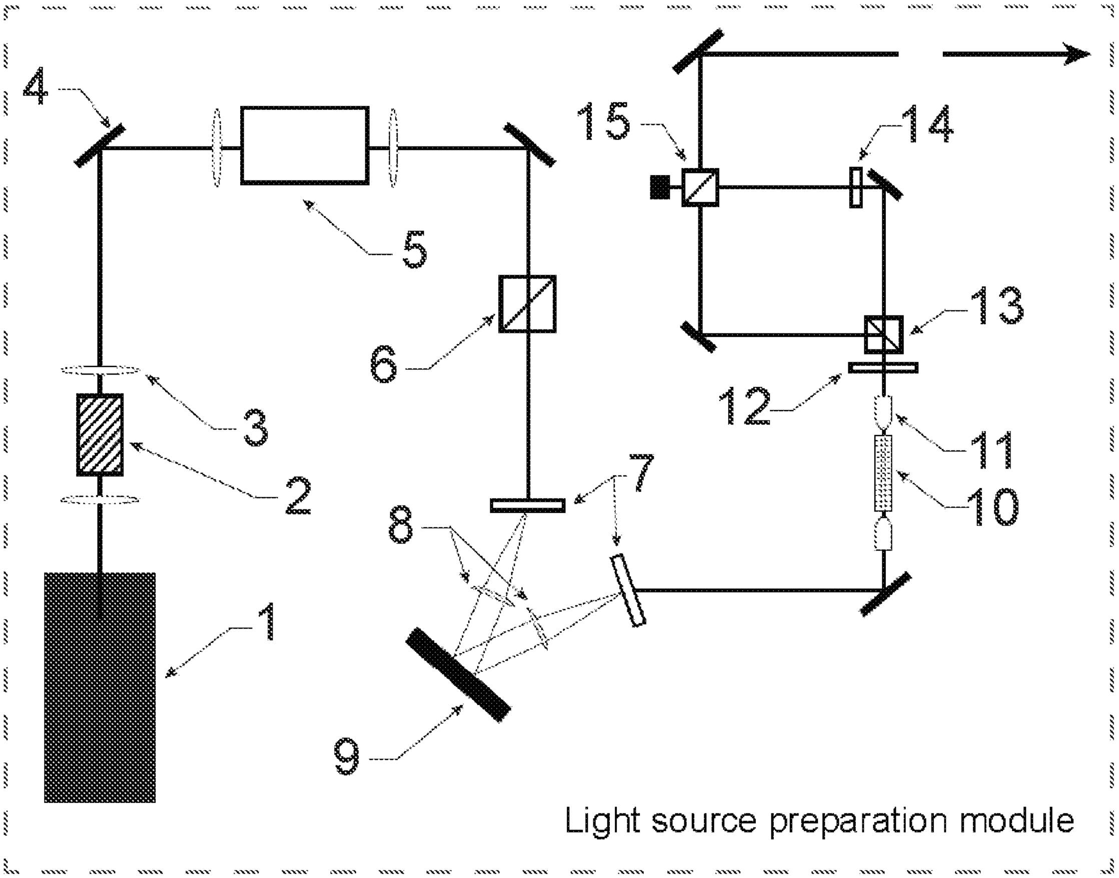
FIG. 2 is a schematic structural diagram of a light source preparation module according to an embodiment of the present application.
Figure 3:
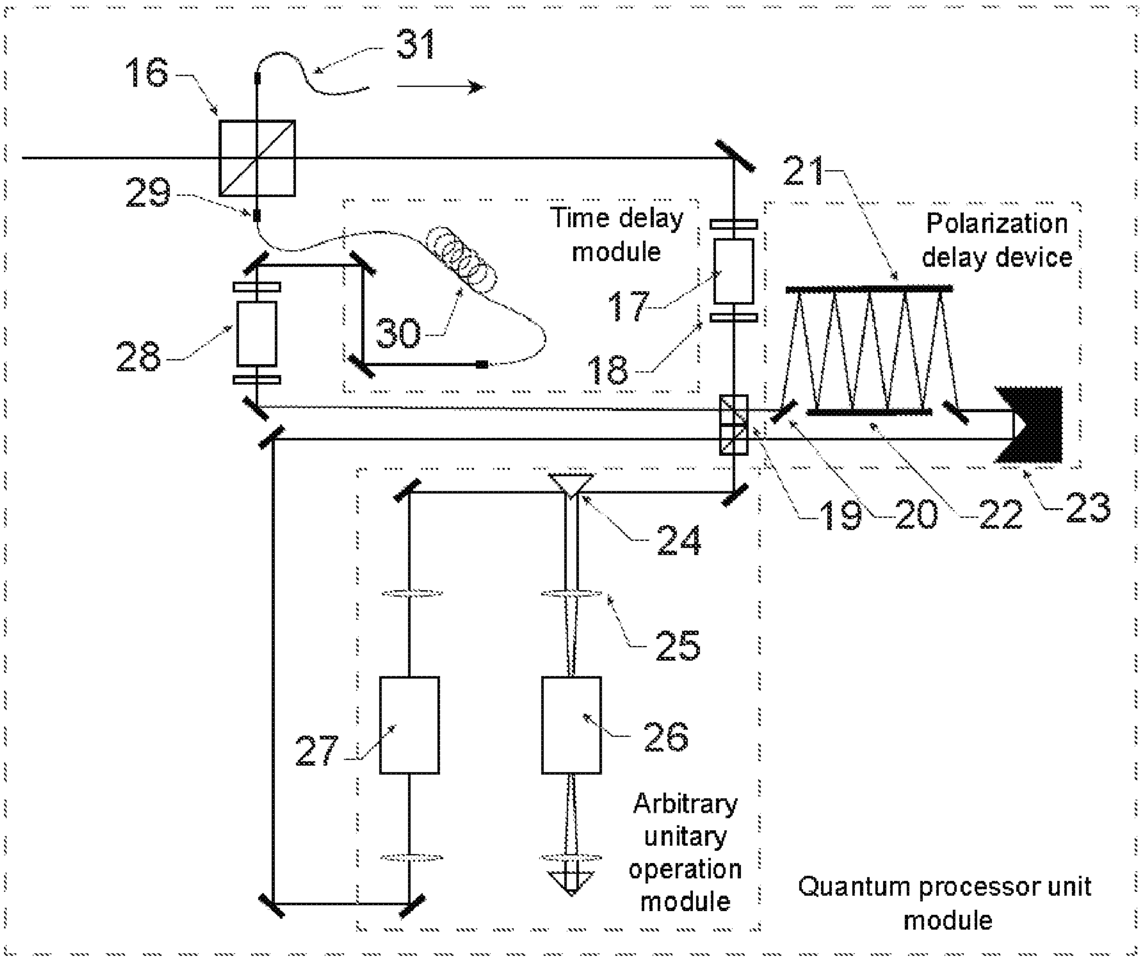
FIG. 3 is a schematic structural diagram of a quantum processing unit module according to an embodiment of the present application.
Figure 4:
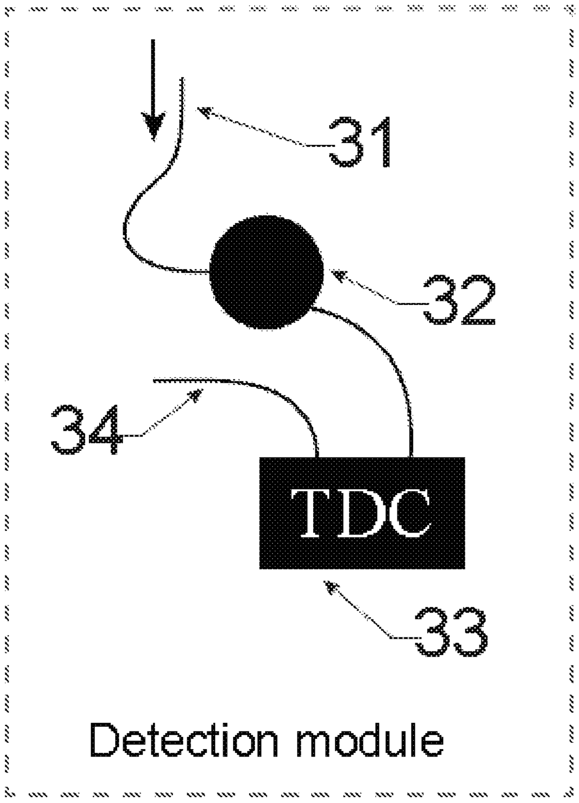
FIG. 4 is a schematic structural diagram of a detection module according to an embodiment of the present application.

As shown in FIG. 2, FIG. 3, and FIG. 4, an embodiment of the present application provides a reverse virtual screening platform based on programmable quantum computing, including a light source preparation module, a quantum processing unit module, a detection module, and a computer; the light source preparation module includes a mode-locked pulse laser light source, an acoustic optical modulator, and a nonlinear crystal; pulse laser generated by the mode-locked pulse laser light source is chopped by the acoustic optical modulator, and the nonlinear crystal is pumped to finally obtain a group of single-mode squeezed vacuum states with different squeezing degrees; the single-mode squeezed vacuum states are delivered into the quantum processing unit module; the quantum processing unit module is a circulating light path where a polarization beam splitter, a first electro-optical modulator, a polarization delay device, an arbitrary unitary operation module, a second electro-optical modulator, and a time delay module are disposed in sequence; the arbitrary unitary operation module is controlled by a programmable arbitrary waveform generator; the quantum processing unit module controls the squeezed states to be continuously evolved in the circulating light path until a high-dimensional unitary operation in any mode is completed, and delivers an evolution-completed squeezed state sequence into the detection module; the detection module measures a photon number in each mode by a superconducting nanowire single-photon detector, and inputs a measurement result into the computer; the computer encodes a task to be a sequence of a string of instructions to control the arbitrary waveform generator, thus controlling a quantum logic gate sequence of the screening platform and realizing a programmable function; and the computer is used for performing real-time display, record and analysis on the photon number detected by the single-photon detector.

The light source preparation module includes a mode-locked pulse laser light source 1; an acoustic optical modulator 2, an electro-optical modulator 5, a first polarization beam splitter 6, a spatial filter composed of a grating 7, a cylindrical lens 8, and a spatial light modulator 9, a nonlinear crystal 10, a filter 12, and a second polarization beam splitter 13 are arranged on a light path of the mode-locked pulse laser light source 1 in sequence; transmitted light passing through the second polarization beam splitter 13 enters a non-polarizing beam splitter 15 via a first half wavelength plate 14; reflected light passing through the second polarization beam splitter 13 directly enters the non-polarizing beam splitter 15 and then enters, after passing through the non-polarizing beam splitter 15, the quantum processing unit module.

In the light source preparation module, first convex lenses 3 are arranged on front and rear light paths of the acoustic optical modulator 2 and the electro-optical modulator 5; objective lenses 11 are arranged on front and rear light paths of the nonlinear crystal 10; and in addition, several silver mirrors used for reflecting light beams and changing directions of the light beams are arranged in the entire light path.

A third polarization beam splitter 16, a first electro-optical modulator 17, a pair of polarization beam splitters 19, a polarization delay device, an arbitrary unitary operation module, a second electro-optical modulator 28, and the time delay module are arranged on the circulating light path of the quantum processing unit module; a squeezed state sequence leaving the circulating light path enters the detection module by an optical fiber 31; and second half wavelength plates 18 are arranged on front and rear light paths of the first electro-optical modulator 17 and the second electro-optical modulator 28. The polarization delay device includes a first silver mirror 20, a second silver mirror 21, a third silver mirror 22, and a corner cube mirror 23. The arbitrary unitary operation module includes a third electro-optical modulator 26 and a fourth electro-optical modulator 27; second convex lenses 25 are arranged on front and rear light paths of the third electro-optical modulator 26 and the fourth electro-optical modulator 27; and a pair of right angle prisms 24 used for changing the direction of a light beam is arranged on the front and rear light paths of the third electro-optical modulator 26. The time delay module includes a long optical fiber 30; and the long optical fiber 30 and the optical fiber 31 are both provided with optical fiber splices 29.

The detection module includes a superconducting single-photon detector 32 connected to the optical fiber 31, and a coincidence instrument 33; and the coincidence instrument 33 is connected to the superconducting single-photon detector 32 and the computer respectively by BNC wires.

In the reverse virtual screening platform based on programmable quantum computing provided in the embodiment, functions of respective components elements are as follows.

The mode-locked pulse laser light source outputs high-energy pulse light to pump the nonlinear crystal, and provides the optical quantum computer system with a light source for preparing the squeezed states.

The convex lens focuses pulse laser into the acoustic optical modulator or the electro-optical modulator.

The acoustic optical modulator is used for selecting a laser pulse to obtain a repetition frequency and pulse number of a desired laser pulse.

The silver mirror is used for reflecting a light beam.

The electro-optical modulator changes the phase of light by applying a tunable voltage. Voltage inputting of the electro-optical modulator is completed by a power amplifier capable of amplifying a digital signal. This kind of power amplifier may make a response to an input TTL signal, and skip from a preset low level to a high level. Quick modulation for the light polarization or phase can be achieved.

The polarization beam splitter splits light beams in different polarizations, that is, transmits the light beams in horizontal polarization and reflects the light beams in vertical polarization.

The grating separates laser spatially according to different frequencies.

The cylindrical lens focuses light in a horizontal direction or vertical direction.

The spatial light modulator applies one phase to light at different spatial positions.

The objective lens focuses light to a waveguide at a shorter working distance.

The nonlinear crystal can generate a corresponding squeezed state under the pumping of the mode-locked pulse laser, so that the optical quantum computer system can complete a Gaussian Boson sampling task. The nonlinear crystal is located on the light source preparation module and is placed behind the mode-locked pulse laser light source.

The filter is used for filtering out pumping laser.

The half wavelength plate is used for rotating the polarization of light in the light path.

The non-polarizing beam splitter reflects (projects) light according to 50:50.

The corner cube mirror reflects light according to an incidence direction on the basis of a small displacement.

The right angle prism (right-angle reflection) reflects light beams at two right angle edges of the prism.

An optical fiber coupling head is mounted in a single-mode optical fiber, or collimates light output by the single-mode optical fiber.

The optical fiber is used as a delay line to achieve a delay effect on the light.

The superconducting single-photon detector is used for detecting single photons at high detection efficiency and also identifying the photon number in one coincidence window.

The BNC wire is used for transmitting an electric signal (transmitting a trigger signal here).

The coincidence instrument (TDC (Time Digital Converter) in the drawing, which mainly realizes a counting function, and is referred to as a coincidence instrument here) achieves coincidence measurement of two single-photon detector signals and is used for analyzing a count of photons in each time window. The coincidence instrument is placed outside a light path of the system and is connected to the single-photon detector or a superconducting photon counting detector by the BNC wire.

The computer is used for: encoding a task to be a sequence of a string of instructions to control the arbitrary waveform generator, thus controlling a quantum logic gate sequence of the quantum computer and realizing a programmable function; performing real-time display, record and analysis on the photon number detected by the single-photon detector; and processing data of a detection result of the coincidence instrument, and analyzing a computation result.

In the light source preparation module, the mode-locked pulse laser light source outputs high-energy pulse light to pump the nonlinear crystal to provide an optical quantum computer system with a light source for preparing the squeezed states, and is located at an initial position of the light source preparation module; the acoustic optical modulator is used for selecting a laser pulse to obtain a repetition frequency and pulse number of a desired laser pulse; the nonlinear crystal can be pumped by the mode-locked pulse laser light source to generate the corresponding squeezed states, so that the optical quantum computer system can complete a Gaussian Boson sampling task; and the nonlinear crystal is placed behind the mode-locked pulse laser light source in the light source preparation module.

A specific preparation method for a squeezed state sequence of the light source preparation module is as follows: chopping the pulse laser generated by the mode-locked pulse laser light source via the acoustic optical modulator to form a sequence composed of n pulses; adjusting the pulse energy of the sequence of these pulses via the electro-optical modulator, and modulating and shaping the spectrum of the sequence via a spatial filter composed of a grating, a cylindrical lens and a spatial light modulator; delivering the sequence finally into the nonlinear crystal to generate corresponding dual-mode squeezed vacuum states; then, performing polarization transformation on the dual-mode squeezed vacuum states, and enabling the dual-mode squeezed vacuum states to become single-mode squeezed vacuum states with the same squeezing degree as the dual-mode squeezed vacuum states; filtering pumped light by the filter; and finally, delivering the squeezed states into the quantum processing unit module. A TTL triggering signal used as a time reference for subsequent light paths can be generated by a signal of a pulse laser device synchronized with a pulse.

In the light source preparation module, a level signal of the pulse laser device that is synchronized with the pulse sequence may be directly used as a time reference for subsequent device regulation and control.

In the quantum processing unit module, the first electro-optical modulator in the circulating light path is used for controlling polarization of light; and the first electro-optical modulator can respectively adjust the polarization of the light to be in a horizontal or vertical state according to a state of the level signal, and further controls various modes of squeezing for entry into the following different light paths to achieve different operations.

The time delay module delays the squeezed state sequence in a corresponding length; and after the evolution of the last mode in the pulse or squeezed state sequence is completed, the sequence enters a next evolution stage to ensure that the evolution is not disordered in timing.

The polarization delay device is used for delaying a vertical or horizontal polarization component in a squeezed state in each mode such that the horizontal and vertical polarization components in the squeezed state sequence are separated and that two adjacent modes may overlap in time after being delayed here, so as to achieve a unitary operation for the two adjacent modes.

The second electro-optical modulator in the circulating light path is used for controlling the number of cycles of the pulse or squeezed state sequence in an annular light path; and by controlling the polarization of the light, the pulse or squeezed state sequence is controlled to continue the evolution in the annular light path or to enter the detection module from the circulating light path.

The arbitrary unitary operation module includes two electro-optical modulators controlled by the arbitrary waveform generator; the arbitrary waveform generator generates a level-tunable signal and inputs the signal into voltage amplifiers which are equipped for the electro-optical modulator and are capable of amplifying an analog signal; the amplifiers linearly amplify the level signal generated by the arbitrary waveform generator, and control the electro-optical modulators to perform continuously tuned phase modulation between two polarizations of a light signal; and the electro-optical modulators can quickly adjust phases of the squeezed states in each mode, and achieve an arbitrary unitary operation between two adjacent modes. A specific implementation method is as follows: crystal axes of the third electro-optical modulator 26 and the fourth electro-optical modulator 27 are respectively rotated to 0 degree and 45 degrees, and phase modulations $\phi_1$ and $\phi_2$ are completed. In this way, a unitary (SU(2)) operation can make light pass through the third electro-optical modulator 26 and the fourth electro-optical modulator 27 to achieve $(SU(2,\varphi)=U_\varphi U_{EOM2=45^\circ}(\phi_2) U_{EOM1=0^\circ}(\phi_1))$, where $U_\varphi$ is an overall phase, which can be compensated in a next cycle. The SU (2) operation formed by the two electro-optical modulators can achieve an n-dimensional arbitrary unitary operation by evolutions of n+1 cycles.

The right angle prism in the arbitrary operation module reflects light which is focused by the convex lens into the electro-optical modulator; emergent light becomes parallel light through the convex lens and is reflected by the right angle prism behind; and the light is focused by the convex lens again into the electro-optical modulator (achieving evolution $U_{EOM1=0^\circ}(\phi_1)$). The emergent light becomes parallel light again via the convex lens, is reflected by the right angle prism again, and is delivered into the subsequent light path; the light is focused via the convex lens again into the electro-optical modulator (achieving evolution $U_{EOM2=45^\circ}(\phi_2)$); and the emergent light becomes parallel light via the convex lens, is reflected by the silver mirror behind, and is delivered into the subsequent light path.

In the detection module, the superconducting nanowire single-photon detector is used for detecting, in response to a single-photon signal, that there are modes with one or more photons after evolution; the coincidence instrument performs coincidence processing on a level detection signal output by the superconducting single-photon detector and a level detection signal output by a photoelectric detector in the light source preparation module or a level synchronization signal output by the pulse laser device; the time of arrival at the detector is changed according to different evolution lengths of the pulse or squeezed state sequence in the annular light source; and during the coincidence processing, the level signal for triggering needs to be delayed for a corresponding duration in a circuit setting.

In a photonic quantum reverse virtual screening platform system, data obtained by detection may be delivered into the computer, and an experimental result is correspondingly processed by a specific program to obtain a molecular docking result.

The superconducting nanowire single-photon detector is connected to two signal input ports of the coincidence instrument respectively, and the level signal generated in the light source preparation module is used for coincidence triggering, so as to reduce the interference of noise; and the coincidence instrument is connected to the computer, and obtains, by means of analyzing whether a photon exists in each time mode, a Gaussian boson sampling computation result.

According to the reverse virtual screening platform based on the programmable quantum computing, in a room-temperature environment, the light path can achieve operations of a single-bit gate and a two-bit controlled NOT gate. Quantum computing tasks such as Gaussian boson sampling, maximum fully connected subgraph searching, and molecular connection can be achieved. According to the quantum reverse virtual screening platform, the molecular connection task can be completed via the Gaussian boson sampling by means of a time domain-based programmable and extensible optical quantum computer system.

An embodiment of the present application further provides a reverse virtual screening method based on programmable quantum computing. For a given micromolecule and a target protein molecule, a binding interaction graph of the compound is computed on a computer according to different distances between pharmacophores. According to an adjacency matrix of the binding interaction graph, the binding interaction graph is encoded into the above-mentioned reverse virtual screening platform based on the programmable quantum computing by decomposing the adjacency matrix. In this way, the Gaussian boson sampling work can be completed by the screening platform, and a maximum fully connected subgraph of the binding interaction graph can be obtained according to a sampling result. Finally, an optimal connection manner for the given micromolecule and the target protein molecule is determined by a structure of the maximum fully connected subgraph, which specifically includes: obtaining all fully connected subgraphs of the binding interaction graph according to the sampling result, and sorting all the fully connected subgraphs according to weights to obtain a fully connected subgraph with a maximum weight, so as to directly determine an optimal connection manner for the micromolecule and the target protein molecule by the structure of the fully connected subgraph with the maximum weight.

The specific process of completing the Gaussian boson sampling work by the screening platform is as follows.

A sequence having a certain number of pulses with a certain repetition frequency is obtained by chopping performed by the acoustic optical modulator. A series of single-mode squeezed vacuum states with different squeezing degrees are obtained by pumping the nonlinear crystal (waveguide ppKTP) under different powers. After being prepared, an input state is delivered to the quantum processing unit module, so that each mode is evolved according to algorithm requirements. The electro-optical modulator equipped with the power amplifier capable of amplifying a digital signal in the annular light path can be used as a high-speed and low-loss light switch or polarization controller, which can determine a depth of evolution and control evolution manners of different polarizations. A high-dimensional unitary evolution operation can always be decomposed into a series of two-dimensional unitary evolution combinations. In the present application, arbitrary unitary evolution between two adjacent modes can be achieved by combining two high-speed and low-loss electro-optical modulators equipped with power amplifiers capable of amplifying an analog signal and two fixed-angle half wavelength plates, and is controlled by the programmable arbitrary waveform generator. By circulation and evolution in the annular light path for multiple times, a high-dimensional global unitary evolution operation can be achieved by an enough number of unitary evolutions between the adjacent modes. After the evolution task is completed, the photon number in each mode can be measured, and the measurement task is completed by a single-photon detector or a superconducting single-photon counting detector. The superconducting single-photon detector is connected to two signal input ports of the coincidence instrument respectively, and a TTL signal generated in the light source preparation module is used for coincidence triggering, to reduce the interference of noise. The coincidence instrument is connected to the computer, and a Gaussian boson sampling computation result is obtained by analyzing whether there are photons in each time mode.

The present application aims to provide a time domain-based photonic quantum computing system, which is utilized to complete the construction of the reverse virtual screening platform based on molecular connection. This set of quantum system can not only be operated at a room temperature and have a relatively small volume, but also can easily extend the quantum encoding dimension to achieve large-scale quantum computing tasks. The light source preparation module is a squeezed-state quantum light source generated by pumping the nonlinear crystal by femtosecond pulse laser; two electro-optical modulators (equipped with power amplifiers capable of amplifying an analog signal) controlled by the programmable arbitrary waveform generator can apply a high-speed tunable phase to each mode on the time domain and achieve a unitary evolution operation in an arbitrary dimension. Finally, the photon numbers in each mode on the time domain are measured with the superconducting nanowire detector. The present application has the advantages of dimension (number of bits) extensibility, programmable control, operation in the room-temperature atmospheric environment, high stability and the like. The time domain-based photonic quantum computing system can well complete the Gaussian boson sampling task; and by means of encoding information of the given micromolecule and the target protein molecule to the quantum computing system, the optimal connection manner for the micromolecule and the target protein molecule can be calculated using the Gaussian boson sampling.

The above descriptions are only the preferred embodiments of the present application, and are not intended to limit the present application. Any modifications, equivalent replacements or improvements, and the like that are made within the spirit and principle of the present application shall fall within the protection scope of the present application.

What is claimed is:

1. A method, comprising:

calculating a binding interaction graph of a molecule and a protein according to distances between pharmacophores;

encoding the binding interaction graph by decomposing an adjacency matrix of the binding interaction graph;

chopping pulse laser by using an acoustic optical modulator, pumping a nonlinear crystal to obtain a group of single-mode squeezed vacuum states with different squeezing degrees according to decomposition of the adjacency matrix, and delivering the single-mode squeezed vacuum states into a circulating light path of a quantum processing unit module;

performing a global unitary evolution operation on the single-mode squeezed vacuum states by electro-optical modulators in the circulating light path to obtain an entangled multi-mode quantum state, and inputting the entangled multi-mode quantum state into a detection module;

measuring a photon number in each mode of the entangled multi-mode quantum state and using the photon number to obtain a sampling result; and obtaining complete subgraphs of the binding interaction graph according to the sampling result, obtaining a complete subgraph with a maximum weight among the complete subgraphs, and determining an optimal connection for the molecule and the protein by a structure of the complete subgraph with the maximum weight.

2. A system, comprising a light source preparation module, a quantum processing unit module, a detection module, and a computer;

wherein the light source preparation module comprises a mode-locked pulse laser light source, an acoustic optical modulator, and a nonlinear crystal;

wherein the acoustic optical modulator is configured to chop a pulse laser generated by the mode-locked pulse laser light source, and the nonlinear crystal is configured to be pumped by the mode-locked pulse laser light source to produce a group of single-mode squeezed vacuum states with different squeezing degrees according to decomposition of an adjacency matrix of a binding interaction graph of a molecule and a protein according to distances between pharmacophores;

wherein the quantum processing unit module configured to receive the single-mode squeezed vacuum states and is a circulating light path where a polarization beam splitter, a first electro-optical modulator, a polarization delay device, an arbitrary unitary operation module, a second electro-optical modulator, and a time delay module are disposed in sequence;

wherein the arbitrary unitary operation module is controlled by a programmable arbitrary waveform generator;

wherein the quantum processing unit module is configured to perform a global unitary evolution operation on the single-mode squeezed vacuum states to produce an entangled multi-mode quantum state;

wherein the detection module is configured to receive the entangled multi-mode quantum state and to measure a photon number in each mode of the entangled multi-mode quantum state; and wherein the computer is configured to produce a sampling result using the photon number, to obtain complete subgraphs of the binding interaction graph according to the sampling result, to obtain a complete subgraph with a maximum weight among the complete subgraphs, and to determine an optimal connection for the molecule and the protein by a structure of the complete subgraph with the maximum weight.

3. The system according to claim 2, wherein the first electro-optical modulator is configured to control polarization.

4. The system according to claim 2, wherein the time delay module is configured to delay the single-mode squeezed vacuum states.

5. The system according to claim 2, wherein the second electro-optical modulator is configured to control a number of cycles of the single-mode squeezed vacuum states in the circulating light path.

* * * * *